United States Patent [19]

Kjellin et al.

[11] Patent Number: 4,548,818
[45] Date of Patent: * Oct. 22, 1985

[54] COMPOSITION AND METHODS FOR THE TREATMENT OF CHRONIC OBSTRUCTIVE AIRWAY DISEASE AND CARDIAC DISEASE USING 3-ALKYLXANTHINES

[76] Inventors: Per G. Kjellin, Spjutgränd 10, 223 75 Lund; Carl G. A. Persson, Slogstorps Molla, 240 33 Löberöd, both of Sweden

[*] Notice: The portion of the term of this patent subsequent to Apr. 20, 1999 has been disclaimed.

[21] Appl. No.: 323,955

[22] Filed: Nov. 23, 1981

[30] Foreign Application Priority Data

Oct. 20, 1978 [SE] Sweden .............................. 7810947

[51] Int. Cl.⁴ ..................... A61K 31/52; C07D 473/06
[52] U.S. Cl. .................................... 514/263; 544/273
[58] Field of Search ................. 544/273, 311; 424/253

[56] References Cited

U.S. PATENT DOCUMENTS

| 2,646,432 | 7/1953 | Homeyer et al. | 544/273 X |
| 2,781,344 | 2/1957 | Comte | 544/311 |
| 2,844,576 | 7/1958 | Goldman et al. | 544/273 |
| 4,089,959 | 5/1978 | Diamond | 424/253 |
| 4,120,947 | 10/1978 | Diamond | 424/45 |
| 4,233,303 | 11/1980 | Bergstrand et al. | 424/253 |
| 4,325,956 | 4/1982 | Kjellin et al. | 424/253 |
| 4,338,319 | 7/1982 | Kjellin et al. | 424/253 |

FOREIGN PATENT DOCUMENTS

| 864868 | 1/1953 | Fed. Rep. of Germany . |
| 1245969 | 8/1967 | Fed. Rep. of Germany . |
| 2323906 | 11/1973 | Fed. Rep. of Germany . |
| 2713389 | 10/1977 | Fed. Rep. of Germany . |
| 683523 | 12/1952 | United Kingdom . |
| 982079 | 2/1965 | United Kingdom . |

OTHER PUBLICATIONS

Persson, et al., Acta pharmacol. et toxicol., vol. 49, pp. 317-320 (1981).
Persson, et al., Life Sciences, vol. 30, pp. 2181-2189 (1982).
Read, et al., Psychopharmacologica, vol. 1, pp. 346-350 (1960).
Ohtsuka, Chemical Abstracts, vol. 78, 124544k (1973).
Ohtuska, Chemical Abstracts, vol. 81, 152277f (1974).
Beavo, et al., Chemical Abstracts, vol. 74, 40820b (1971).
Kramer, et al., Chemical Abstracts, vol. 87, 98027h (1977).
LeRoy, J. Pharmacol. Exptl. Therap., 69, pp. 45-51 (1940).
Goldner, et al., Ann. Chem. 691, pp. 142-158 (1966).
Kattus, et al., Bull. Johns Hopkins Hospital (Balt.), 89, 1-8 (1951).

Primary Examiner—Paul M. Coughlan, Jr.
Assistant Examiner—Diana G. Rivers

[57] ABSTRACT

Compounds having activity against chronic obstructive airway disease or cardiac disease, characterized by the formula

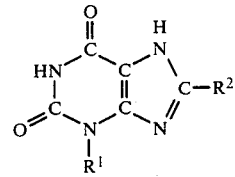

wherein $R^1$ is n-propyl, n-butyl, isobutyl, n-pentyl, 2-methylbutyl, 3-methylbutyl, 2,2-dimethylpropyl, cyclopropyl, cyclobutyl, cyclopentyl or cyclohexylmethyl, and $R^2$ is hydrogen or methyl, provided that $R^2$ is methyl when $R^1$ is n-propyl, n-butyl or isobutyl, or a physiologically acceptable salt thereof.

8 Claims, 1 Drawing Figure

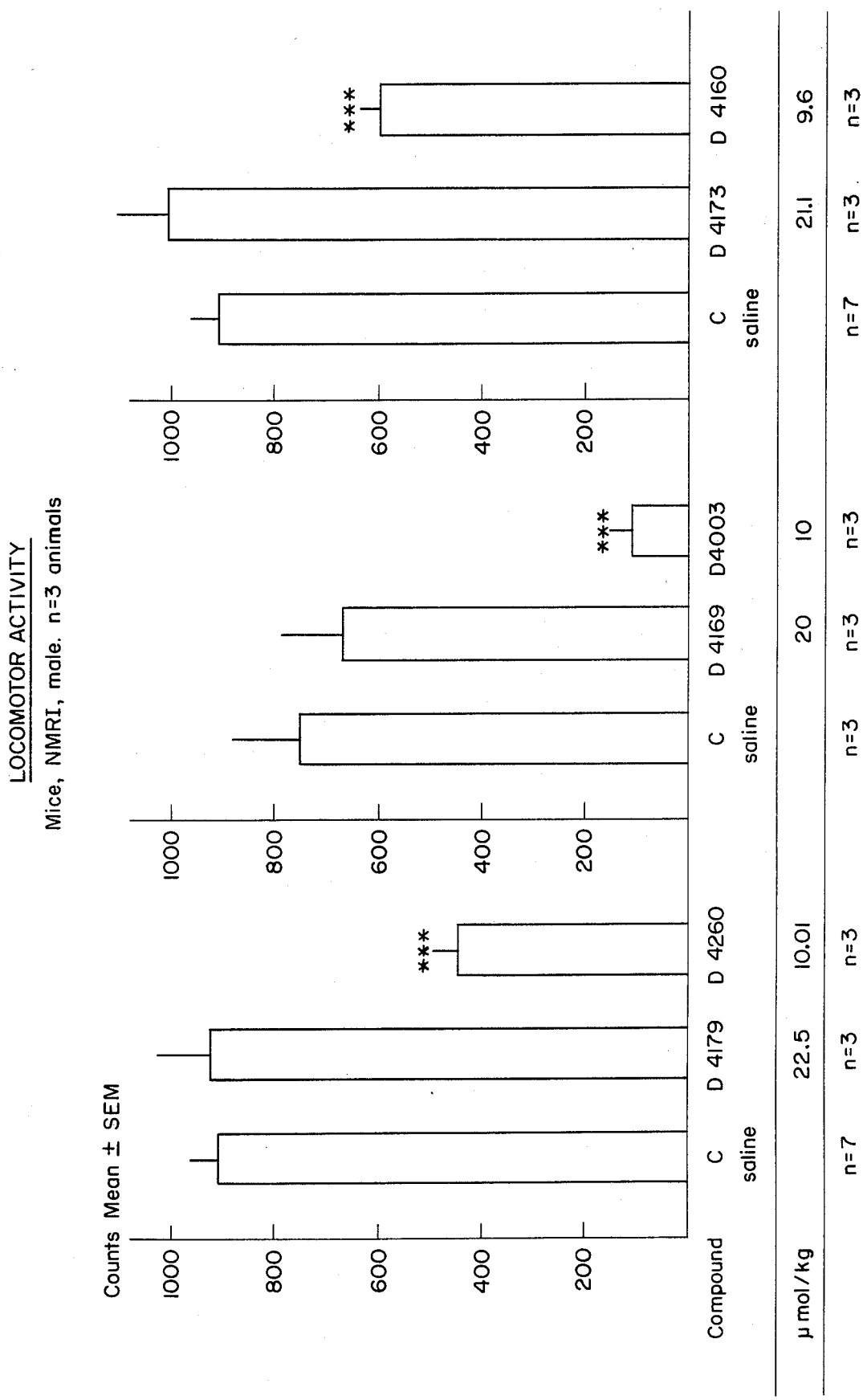

COMPOSITION AND METHODS FOR THE TREATMENT OF CHRONIC OBSTRUCTIVE AIRWAY DISEASE AND CARDIAC DISEASE USING 3-ALKYLXANTHINES

BACKGROUND OF THE INVENTION

The present invention relates to novel, pharmacologically active compounds, methods and intermediates for their preparation and their therapeutical use. The invention also relates to pharmaceutical compositions containing the compounds. More particularly, the novel compounds of the invention are intended for the treatment of chronic obstructive airway disease (COAD) or cardiac disease.

The object of the present invention is to provide xanthine derivatives which have a bronchodilatory and cardiotonic potency but which do not elicit convulsions.

Theophylline and various salts thereof are used in the treatment of chronic obstructive airway disease (COAD) and cardiac disease. Major therapeutic effects of theophylline are to relax bronchial smooth muscle and stimulate heart muscle. The major drawback with theophylline therapy is that the drug frequently produces toxic side-effects; most common are nausea and gastric distress, most serious are convulsions, which may lead to death.

Another object of the present invention is to provide xanthine derivatives which have a bronchodilatory and cardiotonic potency but which do not produce drowsiness.

Certain xanthine derivatives, in particular the 1,3,8-trialkylxanthines having a 1-methyl group combined with a group having 4–7 carbon atoms in the 3-position, are used in the treatment of bronchial asthma and other bronchospastic and allergic diseases. The major drawback with 1,3,8-trialkylxanthine therapy is that such drugs frequently produce behavioral side-effects, such as drowsiness. Thus, a patient so treated must cope with an impaired level of alertness. In these instances, operation of heavy machinery or driving a car would be contraindicated.

SUMMARY OF THE INVENTION

It has been found according to the present invention that compounds of the formula

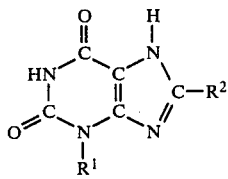

and the physiologically acceptable salts thereof, wherein $R^1$ is n-propyl, n-butyl, isobutyl, n-pentyl, 2-methylbutyl, 3-methylbutyl, 2,2-dimethylpropyl, cyclopropyl, cyclobutyl, cyclopentyl or cyclohexylmethyl, and $R^2$ is hydrogen or methyl, provided that $R^2$ is methyl when $R^1$ is n-propyl, n-butyl or isobutyl, possess bronchodilatory and cardiotonic potency but do not elicit convulsions or cause drowsiness. These advantageous properties make the compounds of the invention valuable in the treatment of chronic obstructive airway disease (COAD) and of cardiac disease.

This invention also takes into consideration that compounds which structurally deviate from the formula (I) after administration to a living organism may be transformed therein to a compound of the formula (I) and in this structural form exerting their effects. This consideration is a further aspect of this invention.

DISCLOSURE OF THE INVENTION

The present invention includes pharmaceutically acceptable salts of compounds of formula (I) with pharmaceutically acceptable bases. The term "pharmaceutically acceptably salts" means salts the cations of which are relatively innocuous to the animal organism when used in therapeutic doses so that the beneficial pharmacological properties of the parent compounds of general formula (I) are not vitiated by side effects ascribable to those cations. Suitable salts include the alkali metal, e.g. sodium and potassium, and ammonium salts and salts of amines known in the art to be pharmaceutically acceptable, e.g. glycine, ethylene diamine, choline, diethanolamine, triethanolamine, octadecylamine, diethylamine, triethylamine, 1-amino-2-propanol-2-amino-2-(hydroxymethyl)propane-1,3-diol and 1-(3,4-dihydroxyphenyl)-2-isopropylaminoethanol.

Pharmaceutically acceptable salts may be prepared by the reaction together of stoichiometric quantities of a compound of formula (I) and the appropriate base, that is to say, a base as described immediately hereinbefore, for example at an elevated temperature, with or without an appropriate solvent, preferably followed by recrystallization from an appropriate solvent, for example a hydroxylic solvent, e.g. water, of the salt so formed.

In clinical practice the compounds of the present invention will normally be administered orally, rectally, nasally, sublingually, by injection or by inhalation in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule, and such preparations comprise a further aspect of the invention. Usually the active substance will comprise between 0.1 and 99% by weight of the preparation, for example between 0.5 and 20% for preparations intended for injection and between 0.1 and 50% for preparations intended for oral administration.

To produce pharmaceutical preparations in the form of dosage units for oral application containing a compound of the invention the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative, polyvinylpyrrolidone or gelatine andh also may include lubricants such as magnesium or calcium stearate or a Carbowax ® or other polyethylene glycol waxes and compressed to form tablets or cores for dragées. If dragées are required, the cores may be coated, for example with concentrated sugar solutions which may contain gum arabic, talc and/or titanium dioxide, or alternatively with a film forming agent dissolved in easily volatile organic solvent or other suitable solvent or mixtures of organic solvents. Dyestuffs can be added to these coatings for example, to distinguish between different contents of active substance. For the preparation of soft gelatine capsules (pearl-shaped closed capsules) consisting of gelatine and, for example, glycerol as a plasticizer, or similar closed capsules, the active substance may be admixed with a Carbowax ® or a suitable oil as e.g. sesame oil, olive oil, or arachis oil. Hard gelatine capsules may contain granulates of the active substance with solid, pulverulent carriers such as lactose, saccharose, sorbitol, mannitol, starches (for example potato starch, corn starch or amylopectin), cellulose derivatives, polyvinylpyrrolidine or gelatine and may also include magnesium stearate of stearic acid as lubricants.

A compound of the invention may also be formulated as a sustained action dosage form using suitable excipients. Different methods may be used for the availability control e.g. diffusion process and ion exchange. Methods using the diffusion process may be exemplified by products involving coated granules or particles, matrix imbedded drug and slightly soluble forms.

Effervescent powders are prepared by mixing the active ingredient with non-toxic carbonates or hydrogen carbonates of e.g. sodium, potassium or calcium, such as calcium carbonate, potassium carbonate and potassium hydrogen carbonate, solid, non-toxic acids such as tartaric acid, ascorbic acid, and citric acid, and for example aroma.

Liquid preparations for oral application may be in the form of elixirs, syrups or suspensions, for example solutions containing from about 0.1% to 20% by weight of active substance, sugar and a mixture of ethanol, water, glycerol, propylene glycol and optionally aroma, saccharine and/or carboxymethylcellulose as a dispersing agent.

For parenteral application by injection preparations may comprise an aqueous solution or suspension of the active substances according to the invention, desirably in a concentration of 0.5–10%, and optionally also a stabilizing agent and/or buffer substances in aqueous solution. Dosage units of the solution may advantageously be enclosed in ampoules.

The dosage at which the active ingredients are administered may vary within a wide range and will depend on various factors such as for example the individual requirements of each patient. A suitable oral dosage range is from 50 to 1000 mg given 1 to 4 times a day. A suitable dosage range at parenteral administration is from 20 to 500 mg.

The pharmaceutical compositions containing the active ingredients may suitably be formulated so that they provide doses within these ranges either as single dosage units or as multiple dosage units.

The compounds of the invention can be prepared by any of the following methods.

A. Reacting a compound of the formula

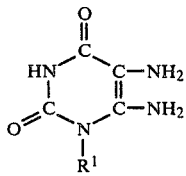

with a compound of the formula

wherein $R^1$ is n-propyl, n-butyl, isobutyl, n-pentyl, 2-methylbutyl, 3-methylbutyl, 2,2-dimethylpropyl, cyclopropyl, cyclobutyl, cyclopentyl, or cyclohexylmethyl, $R^2$ is hydrogen or methyl, X is —COOH, —CONH$_2$ or —OC—O—CO—$R^2$, provided that $R^2$ is methyl when $R^1$ is n-propyl, n-butyl or isobutyl and, if necessary, submitting the obtained product to dehydration.

The dehydration may be carried out for instance by heating the reaction mixture in the absence of solvent or by heating the mixture with alkali or by boiling the mixture in a high-boiling solvent.

The starting material of the compounds prepared according to this route can be obtained for instance as illustrated in the reaction scheme below, wherein the radical $R^1$ has the meaning given in this specification.

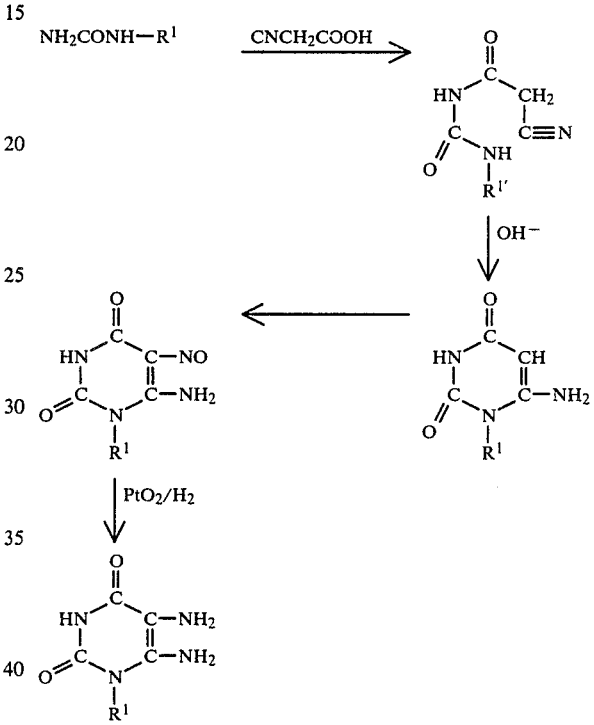

B. Reacting a compound of the formula

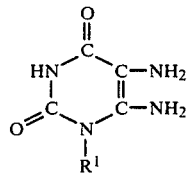

with a compound of the formula

wherein $R^1$ is n-propyl, n-butyl, isobutyl, n-pentyl, 2-methylbutyl, 3-methylbutyl, 2,2-dimethylpropyl, cyclopropyl, cyclobutyl, cyclopentyl, or cyclohexylmethyl, $R^2$ is hydrogen or methyl, $X^1$ is —CHO or

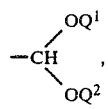

provided that $R^2$ is methyl when $R^1$ is n-propyl, n-butyl or isobutyl, and submitting the obtained product to oxidative cyclization.

$Q^1$ is hydrogen or an alkyl group with 1–3 carbon atoms and $Q^2$ is an alkyl group with 1–3 carbon atoms. Preferably $Q^1$ and $Q^2$ are methyl or ethyl.

For the oxidative cyclization a variety of agents can be used, e.g. thionyl chloride, $SOCl_2$.

C. Reacting a compound of the formula

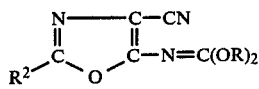

with a compound of the formula

wherein $R^1$ is n-propyl, n-butyl, or n-pentyl, $R^2$ is hydrogen or methyl, R is a lower alkyl group (with 1–3 carbon atoms), provided that $R^2$ is methyl when $R^1$ is n-propyl or n-butyl, and submitting the obtained product to a basic medium.

By this method compounds of the formula 1 wherein $R^1$ is n-propyl, n-butyl or n-pentyl, $R^2$ is hydrogen or methyl, provided that $R^2$ is methyl when $R^1$ is n-propyl or n-butyl are obtained.

The compounds useful as an intermediate for the preparation of therapeutically active xanthine derivatives, which intermediates are characterized by the formula

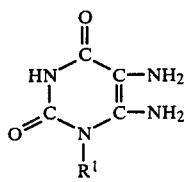

wherein $R^1$ is n-pentyl, 2-methylbutyl, 3-methylbutyl, 2,2-dimethylpropyl, cyclopropyl, cyclobutyl, cyclopentyl or cyclohexylmethyl are not previously described in the literature. They are valuable starting materials for the preparation via methods A and B of the compounds of the invention. The preparation of the starting material is described in connection with the description of method A.

The best result when carrying out this invention will be obtained when the compound 3-cyclopentyl-3,7-dihydro-1H-purine-2,6-dione is used.

The new xanthine derivatives are illustrated further in the following examples. In addition, examples directed to the pharmacological effects of the xanthine derivatives are included.

EXAMPLE 1

Preparation of 3-cyclopropyl-3,7-dihydro-1H-purine-2,6-dione VI (a) Preparation of 6-amino-1-cylopropyl-2,4-(1H,3H)-pyrimidinedione II To a solution of 64 g (0.75 mol) cyanoacetic acid and 250 ml of acetic anhydride was added 70 g (0.7 mol) of cyclopropylurea. The solution was stirred at 60°–70° C. for 2 hours. After cooling white crystals were filtered off and washed with ethanol. Yield 76.7 g (66%) (I). This was suspended in 200 ml of hot water and 55 ml of 5N NaOH was added in portions so the solution the whole time was basic. The reaction mixture was refluxed for 20 minutes and then neutralized with 5N HCl. After cooling, white crystals were filtered off. Yield 31.7 g (42%) (II) NMR.

(b) Preparation of 6-amino-1-cyclopropyl-5-nitroso-2,4-(1H,3H)-pyrimidinedione III 31.7 g (0.19 mol) of 6-amino-1-cyclopropyl-2,4-(1H,3H)-pyrimidinedione (II) was suspended in 250 ml water. To this was added 45 ml of 5N HCl and 15 g of $NaNO_2$ (0.22 mol) which was dissolved in water. The reaction mixture was stirred for 2 hours and after cooling, the red crystals were filtered off and washed with water. Yield 31.9 g (86%) (III) NMR.

(c) Preparation of 1-cyclopropyl-5,6-diamino-2,4-(1H,3H)-pyrimidinedione IV 15.9 g of 6-amino-1-cyclopropyl-5-nitroso-2,4-(1H,3H)-pyrimidinedione (III) was catalytically hydrogenated in 1 liter of DMF and in the presence of 0.1 g $PtO_2$ for 4 hours and at room temperature and at a pressure of 200 kPa. The catalyst and the crystals were filtered off and washed with ethanol. Yield 12.9 g (87%) (IV).

(d) Preparation of 3-cyclopropyl-3,7-dihydro-1H-purine-2,6-dione VI

A solution of 12 g of 1-cyclopropyl-5,6-diamino-2,4-(1H,3H)-pyrimidinedione (IV) in 50 ml of formic acid was refluxed for 2 hours. The hot solution was filtered and 30 ml of chloroform was added and ether was then added slowly. The received crystals were filtered off. Yield 11.2 g (V). The amide (V) was refluxed in 40 ml of 2N NaOH for 1 hour and then neutralized with 5N HCl. The crystals were filtered off. Yield 7 g (60%) (VI) NMR (see Table I).

Reaction scheme:

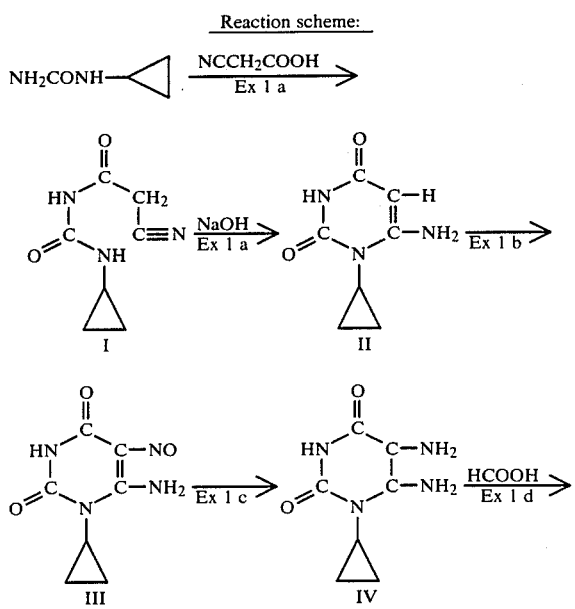

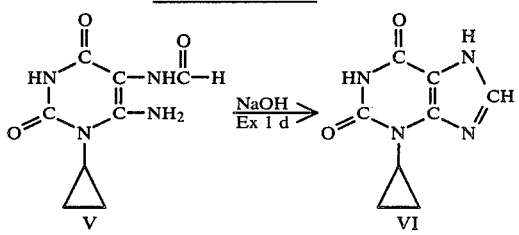

EXAMPLE 2

Preparation of
3-cyclobutyl-3,7-dihydro-1H-purine-2,6-dione XII (a) Preparation of
6-amino-1-cyclobutyl-2,4-(1H,3H)-pyrimidinedione VIII To a solution of 30 g (0.35 mol) cyanoacetic acid and 100 ml of acetic anhydride was added 36.1 g (0.32 mol) of cyclobutylurea. The solution was stirred at 60°-70° C. for 2 hours. After cooling, white crystals were filtered off and washed with ethanol. Yield 36.4 g (63%) (VII). This was suspended in 100 ml of hot water and 50 ml of 2N NaOH was added in portions so the solution the whole time was basic. The reaction mixture was refluxed for 20 minutes. After cooling, white crystals were filtered off. Yield 3.6 g (20%) (VIII) NMR.

(b) Preparation of
6-amino-1-cyclobutyl-5-nitroso-2,4-(1H,3H)-pyrimidinedione IX 3 g (0.0166 mol) of 6-amino-1-cyclobutyl-2,4-(1H,3H)-pyrimidinedione (VIII), was suspended in 25 ml water. To this was added 4 ml of 5N HCl and 1.3 g of NaNO$_2$ (0.019 mol) which was dissolved in water. The reaction mixture was stirred for 3 hours and the red crystals were filtered off and washed with water. Yield 3.1 g (89%) (IX) NMR.

(c) Preparation of
1-cyclobutyl-5,6-diamino-2,4-(1H,3H)-pyrimidinedione X 6.9 g of 6-amino-1-cyclobutyl-5-nitroso-2,4-(1H,3H)-pyrimidinedione (IX) was catalytically hydrogenated in 250 ml of DMF and in the presence of 0.1 g PtO$_2$ for 2 hours and at room temperature and at a pressure of 200 kPa. The catalyst and the crystals were filtered off and washed with ethanol. Yield 3.5 g (54%) (X).

(d) Preparation of
3-cyclobutyl-3,7-dihydro-1H-purine-2,6-dione XII

A solution of 3.5 g of 1-cyclobutyl-5,6-diamino-2,4-(1H,3H)-pyrimidinedione (X) in 20 ml of formic acid was refluxed for 2 hours. The hot solution was filtered and 20 ml of chloroform was added and ether was then added slowly. The received crystals were filtered off. Yield 2.7 g (XI).

The amide (XI) was refluxed in 20 ml of 2N NaOH for 1 hour and then neutralized with 5N HCl. The crystals were filtered off and recrystallized from 150 ml ethanol. Yield 1.4 g (38%) (XII) NMR (see Table I).

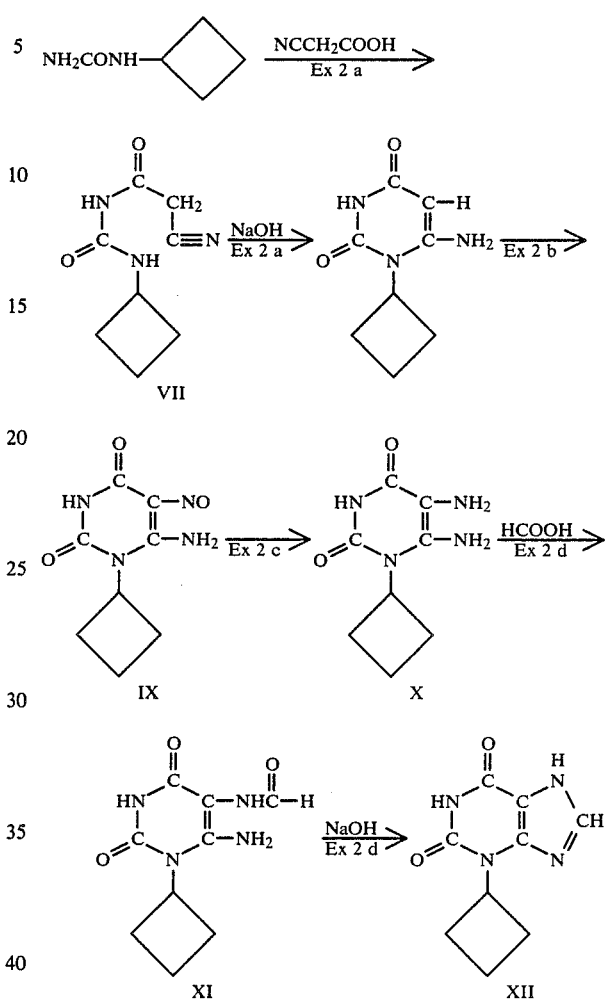

EXAMPLE 3

Preparation of
3-cyclopentyl-3,7-dihydro-1H-purine-2,6-dione XVIII (a) Preparation of
6-amino-1-cyclopentyl-2,4-(1H,3H)-pyrimidinedione XIV To a solution of 136 g (1.6 mol) cyanoacetic acid and 400 ml of acetic anhydride was added 192 g (1.5 mol) of cyclopentylurea. The solution was stirred at 60°-70° C. for 2 hours. After cooling white crystals were filtered off and washed with ethanol. Yield 192 g (66%) (XIII). This was stirred in 500 ml of hot water and 195 ml of 5N NaOH was added in portions so the solution the whole time was basic. The reaction mixture was refluxed for 20 minutes and then neutralized with 5N HCl. After cooling, white crystals of cyclopentylurea were filtered off (159 g). The filtrate was evaporated and the residue was refluxed with 200 ml of 1N NaOH. After cooling the cyclopentylurea was filtered off and the filtrate was neutralized with 5N HCl. The crystals were filtered off. Yield 3.8 g (2%) (XIV) NMR.

(b) Preparation of 6-amino-1-cyclopentyl-5-nitroso-2,4-(1H,3H)-pyrimidinedione XV 12.4 g (0.064 mol) of 6-amino-1-cyclopentyl-2,4-(1H,3H)-pyrimidinedione (XIV) was suspended in 200 ml water. To this was added 14 ml of 5N HCl and 4.8 g of $NaNO_2$ (0.07 mol) which was dissolved in water. The reaction mixture was stirred for 1 hour and washed with water. Yield 12.9 g (90%) (XV) NMR.

(c) Preparation of 1-cyclopentyl-5,6-diamino-2,4-(1H,3H)-pyrimidinedione XVI 12.9 g of 6-amino-1-cyclopentyl-5-nitroso-2,4-(1H,3H)-pyrimidinedione (XV) was catalytically hydrogenated in 30 ml of 2N HCl and in the presence of 0.1 g $PtO_2$ for 3 hours and at room temperature and at a pressure of 200 kPa. The catalyst was filtered off and the filtrate was neutralized with 5N NaOH. The crystals were filtered off. Yield 6.1 g (50%) (XV).

(d) Preparation of 3-cyclopentyl-3,7-dihydro-1H-purine-2,6-dione XVIII

A solution of 6.1 g of 1-cyclopentyl-5,6-diamino-2,4-(1H,3H)-pyrimidinedione (XVI) in 25 ml of formic acid was refluxed for 1 hour. The hot solution was filtered and 20 ml of chloroform was added and ether was then added slowly. The received crystals were filtered off. Yield 5.9 g (XVII).

The amide (XVII) was refluxed in 30 ml of 2N NaOH for 1 hour and then neutralized with 5N HCl. The crystals were filtered off and recrystallized from 400 ml ethanol. Yield 3.4 g (53%) (XVIII) NMR (see Table I).

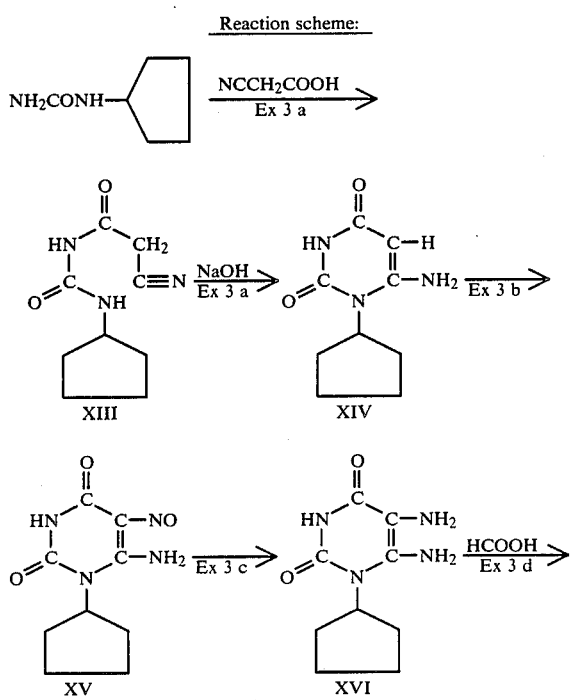

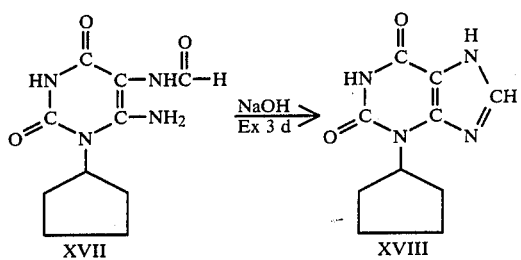

EXAMPLE 4

Preparation of 3,7-dihydro-cyclohexylmethyl-1H-purine-2,6-dione XXIV (a) Preparation of 6-amino-1-cyclohexylmethyl-2,4-(1H,3H)-pyrimidine-dione (XX) was performed according to the description of Example 3a.

(b) Preparation of 6-amino-1-cyclohexylmethyl-5-nitroso-2,4-(1H,3H)-pyrimidinedione (XXI) was performed according to the description of Example 3b.

(c) Preparation of 5,6-diamino-1-cyclohexylmethyl-2,4-(1H,3H)-pyrimidinedione (XXII) was performed according to the description of Example 2c.

(d) Preparation of 3,7-dihydro-3-cyclohexylmethyl-1H-purine-2,6-dione XXIV 2 g of 5,6-diamino-1-cyclohexylmethyl-2,4-(1H,3H)-pyrimidine dione (XXII) was refluxed in 10 ml of formic acid for 1 h. 5 ml of chloroform was added and ether was then added slowly. The received crystals were filtered off. Yield 2.1 g (XXIII). The amide (XXIII) was refluxed in 15 ml of 2N NaOH for 1 hour and then neutralized with 5N HCl. Yield 1.7 g (XXIV) NMR (see Table I).

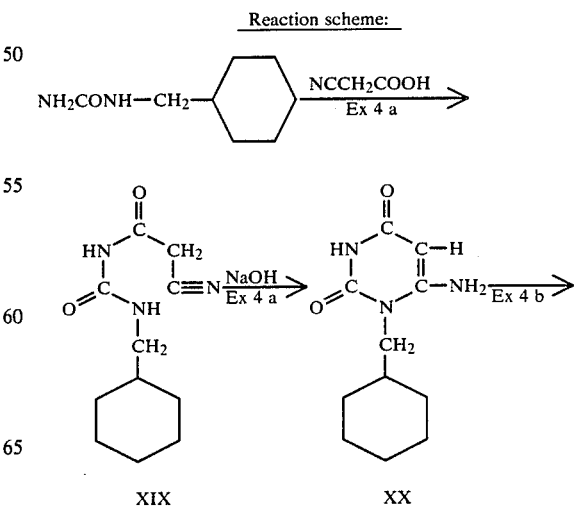

-continued
Reaction scheme:

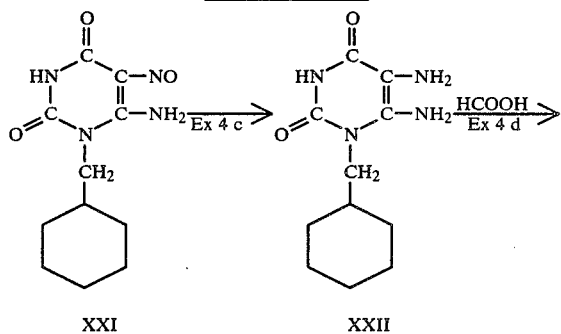

XXI    XXII

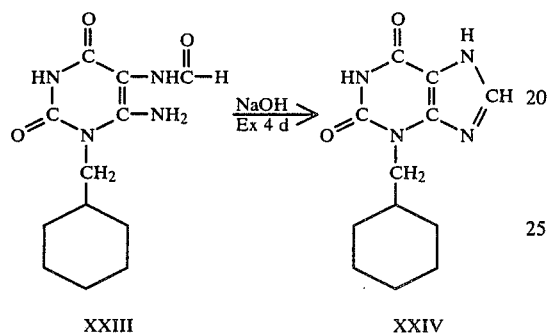

XXIII    XXIV

EXAMPLE 5

Preparation of 3,7-dihydro-3-(2,2-dimethylpropyl)-1H-purine-2,6-dione XXIX (a) Preparation of 6-amino-1-(2,2-dimethylpropyl)-2,4-(1H,3H)-pyrimidinedione (XXVI) was performed according to the description of Example 3a.

(b) Preparation of 6-amino-1-(2,2-dimethylpropyl)-5-nitroso-2,4-(1H,3H)-pyrimidine dione (XXVII)

To a solution of 7.0 g of XXVI in 50 ml of DMSO was added 8 ml of 5N HCl and 2.7 g of NaNO₂ dissolved in 5 ml of water. The reaction mixture was stirred 10 minutes at 50° C. and then 100 ml of water was added. The red crystals were filtered off. Yield 6 g (XXVII).

(c) Preparation of 5,6-diamino-1-(2,2-dimethylpropyl)-2,4-(1H,3H)-pyrimidinedione (XXVIII)

To a suspension of 6.0 g of XXVII in 100 ml of water was added 13.0 g of sodiumdithionite in portions. The green crystals were filtered off and washed with water. Yield 4.0 g (XXVIII).

(d) Preparation of 3,7-dihydro-3-(2,2-dimethylpropyl)-1H-purine-2,6-dione (XXIX)

4.0 g of XXVIII was refluxed in 20 ml of formamide for 30 minutes. After cooling 30 ml of ethanol was added and the yellow crystals were filtered off and recrystallized from 15 ml of DMF. Yield 2.0 g (XXIX) NMR (see Table I).

Reaction scheme:

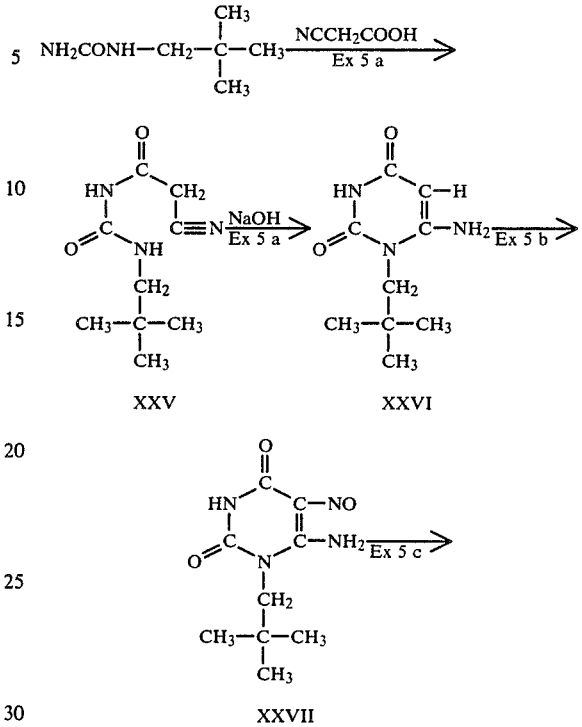

XXV    XXVI

XXVII

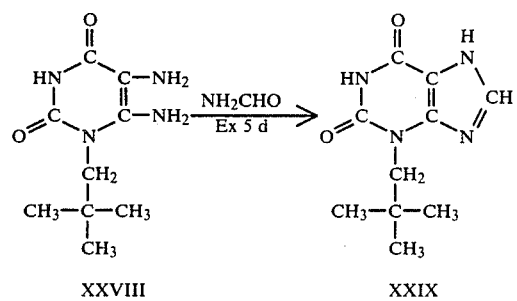

XXVIII    XXIX

EXAMPLE 6

Preparation of 3,7-dihydro-8-methyl-3-cyclohexylmethyl-1H-purine-2,6-dione XXX 1 g of 5,6-diamino-1-cyclohexylmethyl-2,4-(1H,3H)-pyrimidine dione (XXII) was refluxed in 5 ml of acetic acid for 1 hour. 2 ml of chloroform was added and ether was then added slowly. The received crystals of the amide were filtered off. Yield 1 g.

The amide was refluxed in 10 ml of 2N NaOH for 1 hour and then neutralized with 5N HCl. The crystals were filtered off and recrystallized from 80 ml of ethanol. Yield 0.6 g (XXX) NMR (see Table I).

EXAMPLE 7

Preparation of 3-cyclopentyl-3,7-dihydro-8-methyl-1H-purine-2,6-dione XXXI 1.6 g of 1-cyclopentyl-5,6-diamino-2,6-(1H,3H)-pyrimidine dione (XVI) was refluxed in 10 ml of acetic acid for 15 min. 10 ml of chloroform was added and ether was then added slowly. The received crystals of the amide were filtered off. Yield 2.0 g.

The amide was refluxed in 5 ml of 2N NaOH for 1 hour and then neutralized with 5N HCl. The crystals were filtered off and recrystallized from 25 ml of 80% ethanol. Yield 0.7 g (XXXI) NMR (see Table I).

EXAMPLE 8

Preparation of 3,7-dihydro-3-(2,2-dimethylpropyl)-8-methyl-1H-purine-2,6-dione XXXIV 10.4 g of 5,6-diamino-1-(2,2-dimethylpropyl)-2,4-(1H,3H)-pyrimidine dione (XXVIII) was refluxed in 75 ml of acetic acid for 1 hour. 50 ml of chloroform was added and ether was then added slowly. The received crystals were filtered off. Yield 11.4 g. The amide was refluxed in 50 ml of 1N NaOH for 1 hour and then neutralized with 5N HCl. Yield 7.2 g (XXXIV). NMR (see Table I).

EXAMPLE 9

Preparation of 3,7-dihydro-8-methyl-3-(2-methylpropyl)-1H-purine-2,6-dione XXXV 10 g of 5,6-diamino-1-(2-methylpropyl)-2,4-(1H,3H)-pyrimidine dione was refluxed in 50 ml of acetic acid for 1 hour. 30 ml of chloroform was added and ether was then added slowly. The received crystals were filtered off. Yield 10.8 g. The amide was refluxed in 30 ml of 2N NaOH for 1 hour and then neutralized with 5N HCl. The crystals were filtered off and recrystallized from 50 ml of acetic acid. Yield 3.3 g. NMR (see Table I).

EXAMPLE 10

Preparation of 3-cyclopropyl-3,7-dihydro-8-methyl-1H-purine-2,6-dione XXXVI

A solution of 6.4 g of 1-cyclopropyl-5,6-diamino-2,4-(1H,3H)-pyrimidinedione (IV) in 20 ml of acetic acid was refluxed for 2 hours. The solution was evaporated. The received oil was refluxed in 40 ml of 2N NaOH and 10 ml of 5N NaOH for 1 hour and then neutralized with 5N HCl. The crystals were filtered off. Yield 1.85 g (26%) (XXXVI) NMR (see Table I).

EXAMPLE 11

Preparation of 3-cyclobutyl-3,7-dihydro-8-methyl-1H-purine-2,6-dione XXXVII

A solution of 2.2 g of 1-cyclobutyl-5,6-diamino-2,4-(1H,3H)-pyrimidinedione (X) in 10 ml of acetic acid was refluxed for 2 hours. The solution was evaporated. The received oil was refluxed in 30 ml of 5N NaOH for 1 hour and then neutralized with 5 N HCl. The crystals were filtered off and recrystallized from 100 ml ethanol. Yield 0.4 g (18%) (XXXVII) NMR (see Table I).

EXAMPLE 12

Preparation of 3,7-dihydro-3-pentyl-1H-purine-2,6-dione XXXVIII (a) Preparation of 6-amino-1-pentyl-2,4-(1H,3H)-pyrimidinedione was performed according to the description of Example 3a.

(b) Preparation of 6-amino-1-pentyl-5-nitroso-2,4-(1H,3H)-pyrimidinedione was performed according to the description of Example 3b.

(c) Preparation of 5,6-diamino-1-pentyl-2,4-(1H,3H)-pyrimidinedione (XXXIX) was performed according to the description of Example 5c.

(d) Preparation of 3,7-dihydro-3-pentyl-1H-purine-2,6-dione XXXVIII 37.4 g of 5,6-diamino-1-pentyl-2,4-(1H,3H)-pyrimidinedione (XXXIX) was refluxed in 50 ml of formic acid for 2 h. 50 ml of chloroform was added and ether was then added slowly. The received crystals were filtered off. Yield 36.8 g. The amide was refluxed in 50 ml of 5N NaOH for 2 hours and then neutralized with 5N HCl. The crystals were filtered off and recrystallized from 1.8 l of ethanol. Yield 18.3 g (XXXVIII) NMR (see Table I).

EXAMPLE 13

Preparation of 3,7-dihydro-8-methyl-3-pentyl-1H-purine-2,6-dione XXXX

A solution of 5 g of 5,6-diamino-1-pentyl-2,4-(1H,3H)-pyrimidinedione (XXXIX) in 15 ml of acetic acid was refluxed for 2 hours. The hot solution was filtered and 15 ml of chloroform was added and ether was then added slowly. The received crystals were filtered off. Yield 5.5 g.

The amide was refluxed in 25 ml of 2N NaOH for 2 hours and then neutralized with 5N HCl. The crystals were filtered off and recrystallized from 225 ml ethanol. Yield 2.1 g (37%) (XXXX) NMR (see Table I).

EXAMPLE 14

Preparation of 3,7-dihydro-3-(2-methyl-1-butyl)-1H-purine-2,6-dione XXXXI (a) Preparation of 6-amino-1-(2-methyl-1-butyl)-2,4-(1H,3H)-pyrimidinedione was performed according to the description of Example 3a.

(b) Preparation of 6-amino-1-(2-methyl-1-butyl)-5-nitroso-2,4-(1H,3H)-pyrimidinedione was performed according to the description of Example 3b.

(c) Preparation of 5,6-diamino-1-(2-methyl-1-butyl)-2,4-(1H,3H)-pyrimidinedione (XXXXII) was performed according to the description of Example 5c.

(d) Preparation of 3,7-dihydro-3-(2-methyl-1-butyl)-1H-purine-2,6-dione XXXXI 17.3 g of 5,6-diamino-1-(2-methyl-1-butyl)-2,4-(1H,3H)-pyrimidinedione (XXXXII) was refluxed in 30 ml of formic acid for 2 h. 20 ml of chloroform was added and ether was then added slowly. The received crystals were filtered off. Yield 17.0 g. The amide was refluxed in 50 ml of 2N NaOH for 2 hours and then neutralized with 5N HCl. The crystals were filtered off and recrystallized from 400 ml of ethanol. Yield 10 g (XXXXI) NMR (see Table I).

EXAMPLE 15

Preparation of 3,7-dihydro-8-methyl-3-(2-methyl-1-butyl)-1H-purine-2,6-dione XXXXIII A solution of 3.2 g of 5,6-diamino-1-(2-methyl-1-butyl)-2,4-(1H,3H)-pyrimidinedione (XXXXII) in 8 ml of acetic acid was refluxed for 2 hours. The hot solution was filtered and 8 ml of chloroform was added and ether was then added slowly. The received crystals were filtered off.

The amide was refluxed in 10 ml of 2N NaOH for 2 hours and then neutralized with 5N HCl. The crystals were filtered off and recrystallized from 75 ml ethanol. Yield 2.0 g (XXXXIII) NMR (see Table I).

EXAMPLE 16

Preparation of 3,7-dihydro-3-(3-methyl-1-butyl)-1H-purine-2,6-dione XXXXIV

A solution of 21 g of 5,6-diamino-1-(3-methyl-1-butyl)-2,4-(1H,3H)-pyrimidinedione in 50 ml of formic acid was refluxed for 2 hours. The hot solution was filtered and 50 ml of chloroform was added and ether was then added slowly. The received crystals were filtered off. Yield 20.2 g.

The amide was refluxed in 25 ml of 5N NaOH for 2 hours and then neutralized with 5N HCl. The crystals were filtered off and recrystallized from 500 ml ethanol. Yield 9.7 g (44%) (XXXXIV) NMR (see Table I).

EXAMPLE 17

Preparation of 3,7-dihydro-8-methyl-3-(3-methyl-1-butyl)-1H-purine-2,6-dione XXXXV A solution of 3.5 g of 5,6-diamino-1-(3-methyl-1-butyl)-2,4-(1H,3H)-pyrimidinedione in 25 ml of acetic acid was refluxed for 2 hours. The hot solution was filtered and 20 ml of chloroform was added and ether was then added slowly. The received crystals were filtered off. Yield 5.2 g.

The amide was refluxed in 25 ml of 2N NaOH for 2 hours and then neutralized with 5N HCl. The crystals were filtered off and recrystallized from 300 ml ethanol. Yield 1.9 g (34%) (XXXXV) NMR (see Table I).

EXAMPLE 18

Preparation of 3,7-dihydro-8-methyl-3-propyl-1H-purine-2,6-dione XXXXVI

A solution of 22.6 g of 5,6-diamino-1-propyl-2,4-(1H,3H)-pyrimidinedione in 50 ml of acetic acid was refluxed for 2 hours. 30 ml of ethanol was added. The received crystals were filtered off. Yield 19.8 g. The amide was refluxed in 80 ml of 2N NaOH for 2 hours and then neutralized with 5N HCl. The crystals were filtered off and recrystallized from 2.1 l ethanol. Yield 9.8 g (38%) (XXXXVI) NMR (see Table I).

EXAMPLE 19

Preparation of 3,7-dihydro-3-butyl-8-methyl-1H-purine-2,6-dione XXXXVII

A solution of 7.6 g of 1-butyl-5,6-diamino-2,4-(1H,3H)-pyrimidinedione in 20 ml of acetic acid was refluxed for 2 hours. The solution was evaporated. The residue was refluxed in 40 ml of 2N NaOH for 2 hours and then neutralized with 5N HCl. The crystals were filtered off and recrystallized from 350 ml ethanol. Yield 1.8 g (21%) (XXXXVII) NMR (see Table I).

TABLE I

NMR data in $\delta$
Solvent DMSO-d6 ($\delta = 2.83$)

| | | $R_3$ | $R_8$ | $N_1H$ | $N_7H$ |
|---|---|---|---|---|---|
| Ex 1d | D 4161 VI | 1H 3,20 m 4H 1,22 m | 1H 8,35s | 11,23b | 13,80b |
| Ex 2d | D 4164 XII | 4H 2,36 m 1H 5,42 p 2H 3,43 p | 1H 8,40s | 11,43b | 13,83b |
| Ex 3d | D 4132 XVIII | 1H 5,53 p 8H 2,17 m | 1H 8,40s | 11,43b | 13,94b |
| Ex 4d | D 4138 XXIV | 2H 4,14 d 11H 1,63 m | 1H 8,37s | 11,37b | 13,90b |
| Ex 5d | D 4034 XXIX | 2H 4,16 s 9H 1,23 s | 1H 8,27s | 11,40b | 13,84b |
| Ex 6 | D 4137 XXX | 2H 4,10 d 11H 1,60 m | 3H 2,70s | 11,27b | 13,45b |
| Ex 7 | D 4134 XXXI | 1H 5,50 p 8H 2,20 m | 3H 2,68s | 11,30b | 13,43b |
| Ex 8 | D 4070 XXXIV | 2H 4,08 s 9H 1,23 s | 3H 2,67s | 11,24b | 13,40b |
| Ex 9 | D 4169 XXXV | 2H 4,05 d 1H 2,50 h 6H 1,10 d | 3H 2,63s | 11,10b | 13,27b |
| Ex 10 | D 4180 XXXVI | 2H 4,20 t 2H 1,95 m 3H 1,13 t | 3H 2,67s | 11,27b | 13,43b |
| Ex 11 | D 4168 XXXVII | 2H 4,22 t 4H 1,77 m 3H 1,08 m | 3H 2,67s | 11,28s | 13,43b |
| Ex 12d | D 4175 XXXVIII | 2H 4,23 t 2H 1,93 p 4H 1,57 m 3H 1,12 t | 1H 8,37s | 11,43b | 13,67b |
| Ex 13 | D 4176 XXXX | 2H 4,20 t 6H 1,70 m 3H 1,13 t | 3H 2,67s | 11,23b | 13,70b |
| Ex 14d | D 4172 XXXXI | 2H 4,13 d 1H 2,27 m 2H 1,50 m 6H 1,10 m | 1H 8,40s | 11,37b | 13,52b |
| Ex 15 | D 4173 XXXXIII | 2H 4,07 d 1H 2,33 m 2H 1,50 m 6H 1,13 m | 3H 2,67s | 11,30s | 13,47b |
| Ex 16d | D 4177 XXXXIV | 2H 4,30 t 2H 1,83 m 1H 1,83 m 6H 1,18 d | 1H 8,33s | 11,37b | 13,60b |
| Ex 17 | D 4178 XXXXV | 2H 4,25 t 2H 1,87 m 1H 1,87 m 6H 1,20 d | 3H 2,70s | 11,27b | 13,40b |
| Ex 18 | D 4167 XXXXVI | 2H 4,05 t 2H 1,98 m 3H 1,10 t | 3H 2,67s | 11,02b | 13,37b |
| Ex 19 | D 4179 XXXXVII | 1H 5,53 p 2H 3,40 m 4H 2,37 m | 3H 2,67s | 11,28s | 13,47b |

The following examples illustrate how the compounds of the invention can be incorporated in pharmaceutical compositions.

EXAMPLE 20

Aerosol for Inhalation

| | |
|---|---|
| Active substance | 1.50 g |
| Miglyol ® | 0.20 g |
| Frigen ® 11/12/113/114 | 100.0 g |

Frigen ® is used to denote the halogenated hydrocarbons. Frigen ® 114 is 1,2-dichloro-1,1,2,2-tetrafluorethane, Frigen ® 113 is 1,1-difluoro-2,2-dichlorotrifluorotrichloroethane, Frigen ® 11 is trichloromonofluoromethane and Frigen ® 12 is dichlorodifluoromethane. Miglyol ® denotes a triglyceride of saturated vegetable oils. For a pulver aerosol, the active substance is mixed with lactose.

EXAMPLE 21

Tablets

Each tablet contains:

| Active substance | 20.0 mg |
|---|---|
| Maize starch | 25.0 mg |
| Lactose | 190.0 mg |
| Gelatin | 1.5 mg |
| Talc | 12.0 mg |
| Magnesium stearate | 1.5 mg |
| | 250.0 mg |

EXAMPLE 22

Suppositories

Each suppository contains:

| Active substance | 50.0 mg |
|---|---|
| Ascorbyl palmitate | 1.0 mg |
| Suppository base (Imhausen H) ad | 2,000.0 mg |

EXAMPLE 23

Injection Solution

| Active substance | 2.000 mg |
|---|---|
| Sodium hydroxide | 0.310 mg |
| Sodium purosulphite | 0.500 mg |
| Disodium edetate | 0.100 mg |
| Sodium chloride | 8.500 mg |
| Sterile water for injection ad | 1.00 g |

EXAMPLE 24

Sublingual Tablets

Each tablet contains:

| Active substance | 20.0 mg |
|---|---|
| Lactose | 85.0 mg |
| Agar | 5.0 mg |
| Talc | 5.0 mg |

PHARMACOLOGICAL TESTS

Acute toxicity studies in mice

Male NMRI mice, weighing 20–26 g. starved for 6 h were used. The compounds, dissolved in 0.5M NaOH and 0.85% NaCl-solution (pH 10.6–12.1) were administered as follows:

(a) intravenously, 0.1 ml/10 g at an injection rate of 0.3 ml per minute (b) orally, 0.1 ml/10 g At least seven dose levels, doses increasing in a geometric progression with a factor 1.2, were examined. Each dose was given to 5 animals. The animals were observed for signs of toxicity during 14 days after administration. The position of extremities in dead animals indicated whether they had died in convulsions or not.

In acute toxicity studies it was observed that many xanthine compounds elicit convulsions. This was also repeatedly shown to occur with theophylline. However, no sign of convulsive activity (such as tonically stretched hindlegs of dead animals) was observed in animals given the compounds of this invention.

Additionally, convulsive activity was studied by slowly infusing drugs into the tail veins of albino mice. In this study it was confirmed that 1-alkyl substituted xanthines (theophylline and caffeine) consistently produced tonic convulsions, and that with the compounds of the invention death occurred without signs of tonic convulsions. (Table II).

Isolated Guinea-Pig Trachea

Guinea-pigs of both sexes, weighing between 150 and 250 g, were killed by a blow on the head and bled. The trachea was removed and cut spirally yielding one or two preparations. The tracheal preparations were mounted in organ baths containing Krebs solution maintained at 37° C. and bubbled with carbogen (95% $O_2$+5% $CO_2$). Isometric tension reflecting the activity in circular tracheal muscle was recorded by means of a force displacement transducer. Initial tension was set at 0.5 g which was the approximate basal tension kept during the experiment. Evaluation of relaxant effects was done when the preparations had contracted to a stable tension by the addition of carbacholine 0.1 µg/ml to the bath. $EC_{50}$ values, i.e. molar concentrations of xanthines required to produce 50% maximum response, were obtained from log concentration response lines and used to calculate the potency of theophylline relative to that of the test drug. After washing out the drugs the trachea resumed its basal tone and was left to stabilize for at least 15 min. before the next drug evaluation was performed. Between two evaluations of theophylline the effect of the test drug was examined and its $EC_{50}$ value was compared with the mean of the previous and following $EC_{50}$ values of theophylline. In the Table II the potency ratios are illustrated. Theophylline is one by definition and a value larger than one indicates that the drug is more potent than theophylline. This study confirmed that the compounds of the invention are significantly more potent than theophylline or caffeine.

Isolated Guinea-Pig Hearts

From the bled guinea-pigs, the hearts were immediately removed and perfused with oxygenated Krebs solution at 37° according to Langendorff. The heart was mounted in a thermostatically controlled organ bath (25 ml) containing Krebs solution. A saline-filled, open-end polyethylene catheter was inserted into the right ventricle through the pulmonary artery. The catheter was fixed to the pulmonary artery by a ligature just above the valvular plane. It was connected to a pressure transducer (P23 AC), making it possible to record changes in intraventricular pressure. From these, the contraction frequency was obtained. Drugs were given as single bolus injections into the perfusion solution. This test showed that the compounds of the invention are significantly more potent than theophylline or caffeine.

TABLE II

| Compound | Guinea-Pig trachea Potency rations of theophylline | Convulsion test mice i.v. Effects | Death mg/kg i.v. | Guinea-Pig heart Potency ratios of theophylline Chronotrop |
|---|---|---|---|---|
| Theophylline | 1 | tonic conv. 30/30 | 446.3 ± 9.6 | 1 |
| Caffeine | 1 | tonic conv. 20/20 | 391.7 ± 17.7 | 0.5 |
| D 4034 XXIX | 3 | loss of balance salivation | 519.1 ± 16.6 | 3 |
| D 4070 XXXIV | 1.8 | loss of balance | 693.3 ± 22.2 | 1.5 |
| D 4138 XXIV | 5 | loss of balance salivation | 543.6 ± 31.7 | 15 |
| D 4137 XXX | 4 | loss of balance salivation | 493.1 ± 19.4 | 10 |
| D 4132 XVIII | 5.65 | loss of balance salivation | 593 ± 21.9 | 3.4 |
| D 4134 XXXI | 5.85 | | | |
| D 4164 XII | 3.8 | loss of balance (clonic/tonic conv. 3/10) | 519.2 ± 16.86 | 2.1 |
| D 4161 VI | 0.5 | single twitches and clonic conv. 1/10 loss of balance | 1030 ± 39.3 | |
| D 4169 XXXV | 10.3 | loss of balance single clonic conv. | 488.2 ± 8.1 | 4 |

VI = 3-cyclopropyl-3,7-dihydro-1H-purine-2,6-dione
XII = 3-cyclobutyl-3,7-dihydro-1H-purine-2,6-dione
XVIII = 3-cyclopentyl-3,7-dihydro-1H-purine-2,6-dione
XXIV = 3,7-dihydro-3-cyclohexylmethyl-1H-purine-2,6-dione
XXIX = 3,7-dihydro-3-(2,2-dimethylpropyl)-1H-purine-2,6-dione
XXX = 3,7-dihydro-8-methyl-3-cyclohexylmethyl-1H-purine-2,6-dione
XXXI = 3-cyclopentyl-3,7-dihydro-8-methyl-1H-purine-2,6-dione
XXXIV = 3,7-dihydro-3-(2,2-dimethylpropyl)-8-methyl-1H-purine-2,6-dione
XXXV = 3,7-dihydro-8-methyl-3-(2-methylpropyl)-1H-purine-2,6-dione

Legend to Table

The left column lists molar potency ratios for bronchodilatation between theophylline and various xanthine compounds. Toxic symptoms occuring before death in mice receiving constant rate infusion of drug i.v. are accounted for in the middle column. Tonic convulsions (conv.) is a consistent effect by theophylline and caffeine (30 out of 30 and 20 out of 20 respectively tested animals had marked tonic convulsions). Each other compound was tested in 10 aminals and in no case a tonic convulsion was induced. The notes indicate, however, that a few animals receiving D 4164, D 4161 or D 4169 exhibited a clonic-type or convulsion or a mixed clonic/tonic type of convulsion, however, of very moderate intensity compared to the effect seen by theophylline and caffeine. The far right column indicates cardiotonic activity as positive chronotropic potency.

Isolated Guinea-Pig Trachea

The guinea-pig trachea were prepared as was discribed previously. Isomeric tension reflecting the activity in circular tracheal muscle was recorded by a force displacement transducer. $EC_{50}$ values, i.e. molar concentrations of xanthines required to produce 50% maximum response, were used to calculate the potency of theophyllin relative to that of the test drug. Theophyllin is one by definition and a value larger than one indicates that the drug is more potent than theophyllin.

The following structures have been prepared and tested:

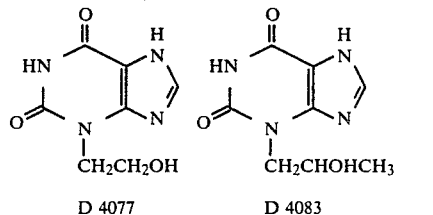

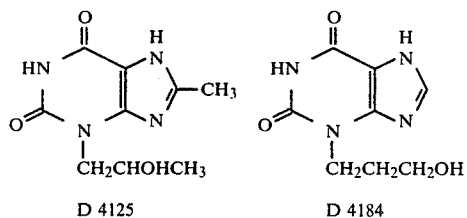

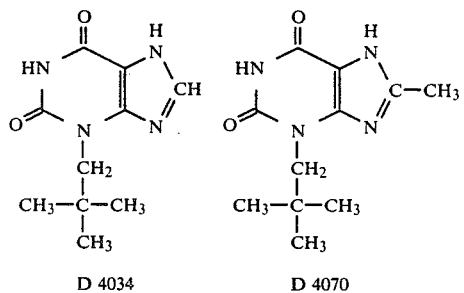

-continued

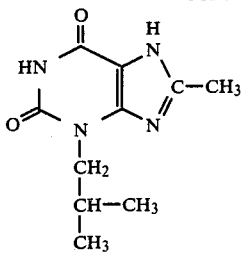

D 4169

Compounds D 4034, D 4070 and D 4169 are Example 5, Exiample 8 and Example 9, respectively of the present application.

In Table III the potency ratios are illustrated. A value larger than one indicates that the drug is more potent than theophylline.

TABLE III

| Guinea-pig Tracheal Preparation | |
|---|---|
| Compound | Potency |
| Theophyllin | 1.0 |
| D 4034 Ex. 5 | 3.0 |
| D 4070 Ex. 8 | 1.8 |
| D 4169 Ex. 9 | 3.3 |
| D 4077 | 0.1 |
| D 4083 | 0.1 |
| D 4125 | 0.4 |
| D 4184 | 0.1 |

Locomotor Activity Studies in Mice

Male NMRI mice, weighing 20 to 26 g, were used. The compounds used had the following structural formula:

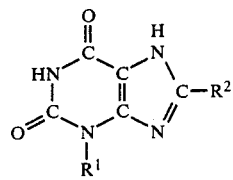

| $R_3$ | $R_1 = H$ | $R_1 = CH_3$ |
|---|---|---|
| —CH$_2$CH$_2$CH$_2$CH$_3$ | D 4179 | D 4260 |
| —CH$_2$CH(CH$_3$)$_2$ | D 4169 | D 4003 |
| —CH$_2$CH(C$_2$H$_5$)(CH$_3$) | D 4173 | D 4160 |

These compounds, dissolved in 0.5M NaOH and 0.85% NaCl-solution (pH 10.6–12.1), were administered intraperitoneally about 30 minutes before the locomotor readings were taken. The doses tested were chosen according to the relative potency on trachea smooth muscle. Each compound was tested in three groups. Referring to FIG. I, the spontaneous motor activity was recorded during the initial active period (5 minutes) after placing the mice in the Motor Activity Meter. The mice treated with compounds of the present invention exhibited locomotor activity which is comparable to the activity of the control mice. The mice treated with 1,3,8-trialkyl xanthines having a 1-methyl group exhibited significantly less locomotor activity. Indeed, these mice exhibited the diminished locomotor activity at a dose level at about 50% of that used with compounds of the present invention.

Appendix
All foreign applications filed more than 12 months prior to the filing date of this application

| Country | Application No. | Date of filing (day, month, year) |
|---|---|---|
| Sweden | 7810947-7 | 20/10/78 |
| Finland | 793224 | 17/10/79 |
| Norway | 793377 | 19/10/79 |
| Denmark | 4321/79 | 12/10/79 |
| EPC | 79850090.6 | 28/09/79 |
| Ireland | 1987/79 | 18/10/79 |
| Australia | 51871/79 | 17/10/79 |
| Canada | 337,077 | 05/10/79 |
| Japan | 135845/79 | 19/10/79 |
| Czechoslovakia | 7082/79 | 18/10/79 |
| East Germany | 216 348 | 19/10/79 |
| Hungary | — | 19/10/79 |
| New Zealand | 191 870 | 17/10/79 |
| South Africa | 79/5113 | 26/09/79 |
| Soviet Union | 2 824 353/04 | 11/10/79 |
| Greece | 60 300 | 19/10/79 |
| Poland | P 219 065 | 19/10/79 |
| Spain | 485 178 | 19/10/79 |
| the Philippines | 23182 | 16/10/79 |
| Portugal | 70 350 | 19/10/79 |
| South Korea | 3567/79 | 15/10/79 |

We claim:

1. A pharmaceutical preparation comprising as active ingredient an effective amount of a compound of the formula

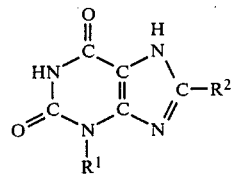

or a physiologically acceptable salt thereof, in which formula $R^1$ is n-propyl, n-butyl, isobutyl, n-pentyl, 2-methylbutyl, 3-methylbutyl, 2,2-dimethylpropyl, cyclopropyl, cyclobutyl, cyclopentyl or cyclohexylmethyl, and $R^2$ is hydrogen or methyl, provided that $R^2$ is methyl when $R^1$ is n-propyl, n-butyl or isobutyl, in association with a pharmaceutically acceptable carrier for use in the treatment of chronic obstructive airway disease.

2. A pharmaceutical preparation comprising as active ingredient an effective amount of a compound of the formula or a physiologically acceptable salt thereof, in which formula $R^1$ is n-propyl, n-butyl, isobutyl, n-pentyl, 2- methylbutyl, 3-methylbutyl, 2,2-dimethylpropyl, cyclopropyl, cyclobutyl, cyclopentyl or cyclohexylmethyl, and R² is hydrogen or methyl, provided that R² is methyl when R¹ is n-propyl, n-butyl or isobutyl, in association with a pharmaceutically acceptable carrier for use in the treatment of cardiac disease.

3. A pharmaceutical preparation according to claim 1 or 2 in dosage unit form.

4. A pharmaceutical preparation according to claim 1 comprising as active ingredient a compound of the formula

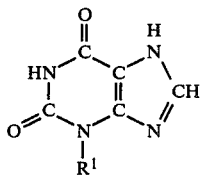

wherein R¹ is n-pentyl, 2-methylbutyl, 3-methylbutyl, 2,2-dimethylpropyl, cyclopropyl, cyclobutyl, cyclopentyl or cyclohexylmethyl; or

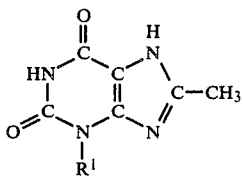

wherein R¹ is n-propyl, n-butyl, isobutyl, n-pentyl, 2-methylbutyl, 3-methylbutyl, 2,2-dimethylpropyl, cyclopropyl, cyclobutyl, cyclopentyl or cyclohexylmethyl, in association with a pharmaceutically acceptable carrier.

5. A pharmaceutical preparation according to claim 2 comprising as active ingredient a compound of the formula

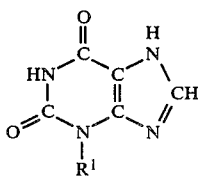

wherein R¹ is n-pentyl, 2-methylbutyl, 3-methylbutyl, 2,2-dimethylpropyl, cyclopropyl, cyclobutyl, cyclopentyl or cyclohexylmethyl; or

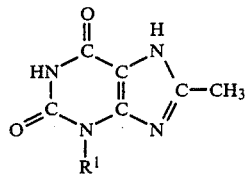

wherein R¹ is n-propyl, n-butyl, isobutyl, n-pentyl, 2-methylbutyl, 3-methylbutyl, 2,2-dimethylpropyl, cyclopropyl, cyclobutyl, cyclopentyl or cyclohexylmethyl, in association with a pharmaceutically acceptable carrier.

6. A pharmaceutical preparation according to claim 4 or 5 in a dosage unit form.

7. A method for the treatment of chronic obstructive airway disease in mammals, including man, characterized in administration to a host in need of such treatment of an effective amount of a compound of the formula

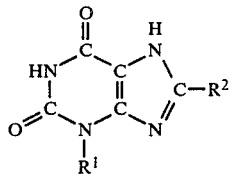

or a physiologically acceptable salt thereof, in which formula R¹ is n-propyl, n-butyl, n-pentyl, 2-methylbutyl, 3-methylbutyl, 2,2-dimethylpropyl, cyclopropyl, cyclobutyl, cyclopentyl or cyclohexylmentyl, and R² is hydrogen or methyl, provided that R² is methyl when R¹ is n-propyl, n-butyl or isobutyl.

8. A method for the treatment of chronic obstructive airway disease according to claim 7 characterized in administering to a host in need of such treatment an effective amount of a compound of the formula

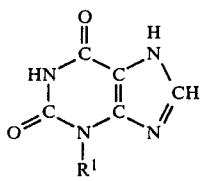

wherein R¹ is n-pentyl, 2-methylbutyl, 3-methylbutyl, 2,2-dimethylpropyl, cyclopropyl, cyclobutyl, cyclopentyl or cyclohexylmethyl; or

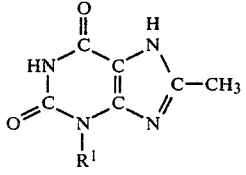

wherein R¹ is n-propyl, n-butyl, isobutyl, n-pentyl, 2-methylbutyl, 3-methylbutyl, 2,2-dimethylpropyl, cyclopropyl, cyclobutyl, cyclopentyl or cyclohexylmethyl.

* * * * *

UNITED STATES PATENT AND TRADEMARK OFFICE
CERTIFICATE OF CORRECTION

PATENT NO. : 4,548,818

DATED : Oct. 22, 1985

INVENTOR(S) : Kjellin et al.

It is certified that error appears in the above-identified patent and that said Letters Patent is hereby corrected as shown below:

<u>First page, following Item 76</u>, insert --[73] Assignee:
Aktiebolaget Draco, Lund, Sweden--;

<u>First page, following Item 22</u>, insert:
--Related U. S. Application Data
[62] Continuation-in-part of Ser. No. 84,440, Oct. 1, 1979, abandoned.--;

<u>First page, 2nd col., just above Item 57 (ABSTRACT)</u>, insert:
--Attorney, Agent, or Firm —
Brumbaugh, Graves, Donohue & Raymond--;

<u>Col. 2, line 56</u>, "andh" should read --and--;

<u>Col. 21, line 15</u>, "Exiample" should read --Example--;

<u>Col. 22, line 6</u>, "at about" should read --of about--; and

<u>Col. 22</u>, delete lines 9 through 31.

Signed and Sealed this

Twenty-fourth Day of June 1986

[SEAL]

Attest:

DONALD J. QUIGG

Attesting Officer

Commissioner of Patents and Trademarks